United States Patent [19]

Fujita

[11] Patent Number: 5,056,035
[45] Date of Patent: Oct. 8, 1991

[54] METHOD FOR PROCESSING INFORMATION ON CHEMICAL REACTIONS

[75] Inventor: Shinsaku Fujita, Minami-ashigra, Japan

[73] Assignee: Fuji Photo Film Co., Ltd., Kanagawa, Japan

[21] Appl. No.: 237,613

[22] Filed: Aug. 25, 1988

Related U.S. Application Data

[63] Continuation of Ser. No. 903,154, Sep. 3, 1986, abandoned.

[30] Foreign Application Priority Data

Sep. 5, 1985 [JP] Japan .................... 60-197463

[51] Int. Cl.$^5$ .......................................... G06F 15/20
[52] U.S. Cl. .................................. 364/497; 364/496
[58] Field of Search .................... 364/500, 497, 496

[56] References Cited

U.S. PATENT DOCUMENTS

| | | | |
|---|---|---|---|
| 3,663,805 | 5/1972 | Carr et al. | 364/500 |
| 3,666,932 | 5/1972 | White | 364/500 |
| 3,814,916 | 6/1974 | Sweeney | 361/500 |
| 4,205,391 | 5/1980 | Ulyanov et al. | 364/496 X |
| 4,473,890 | 9/1984 | Araki | 364/900 |
| 4,642,762 | 2/1987 | Fisanick | 364/300 |
| 4,982,338 | 1/1991 | Fujita | 364/496 X |

OTHER PUBLICATIONS

"The Description of Organic Reactions Based on Imaginary Transition Structures", *Pure and Applied Chem.*, vol. 61, No. 3, pp. 605–608 ('89) Brochure: The Essence of ITS and Connection Table Using Complex Bond Number.
Flow Charts 1–4 *Journal of Synthetic Organic Chemistry, Japan*, vol. 47, No. 5 ('89) English Translation of Japanese Article Written by Applicant.
Roger Attias, DARC Substructure Search System, J. Chem. Inf. Comput. Sci., vol. 23, #3, 1983.
Darc System Pamphlet distributed at A.C.S. meeting Aug., 1983 by Questel inc. in Washington, D.C.
"Modern Approaches to Chemical Reaction Searching", pp. 202–220, Do We Still Need a Classification of Reactions?, by G. Vladutz.
Pages 240–256 "Compound–Oriented and Reaction Structural Langues for Reaction Data Base Management", J. E. DuBois et al.
"Classifications of Reactions by Electron Shift Patterns", pp. 2–9 J. Brandy et al. Chemica Scripta.

*Primary Examiner*—Leo P. Picard
*Assistant Examiner*—Paramita Ghosh
*Attorney, Agent, or Firm*—Sixbey, Friedman, Leedom & Ferguson

[57] ABSTRACT

A method for processing information of chemical reactions of producing at least one product from at least one starting material, said information being given in the form of imaginary transition structures (ITS) in which the starting material is topologically superposed upon the product and bonds are distinguished and classified into three categories of (1) bonds linking two nodes appearing both in the starting and product stages, (2) bonds linking two nodes appearing only in the starting stage and (3) bonds linking two nodes appearing only in the product stage and/or in the form of connection tables of ITS, which comprises extracting from the imaginary transition structure and/or the connection table a reaction string composed of said bonds (2) and said bonds (3) which are alternately arranged to each other.

7 Claims, 1 Drawing Sheet

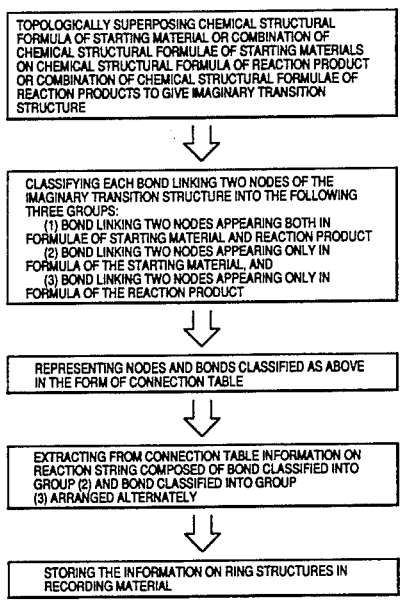

FIG. 1

TOPOLOGICALLY SUPERPOSING CHEMICAL STRUCTURAL FORMULA OF STARTING MATERIAL OR COMBINATION OF CHEMICAL STRUCTURAL FORMULAE OF STARTING MATERIALS ON CHEMICAL STRUCTURAL FORMULA OF REACTION PRODUCT OR COMBINATION OF CHEMICAL STRUCTURAL FORMULAE OF REACTION PRODUCTS TO GIVE IMAGINARY TRANSITION STRUCTURE

CLASSIFYING EACH BOND LINKING TWO NODES OF THE IMAGINARY TRANSITION STRUCTURE INTO THE FOLLOWING THREE GROUPS:
   (1) BOND LINKING TWO NODES APPEARING BOTH IN FORMULAE OF STARTING MATERIAL AND REACTION PRODUCT
   (2) BOND LINKING TWO NODES APPEARING ONLY IN FORMULA OF THE STARTING MATERIAL, AND
   (3) BOND LINKING TWO NODES APPEARING ONLY IN FORMULA OF THE REACTION PRODUCT

REPRESENTING NODES AND BONDS CLASSIFIED AS ABOVE IN THE FORM OF CONNECTION TABLE

EXTRACTING FROM CONNECTION TABLE INFORMATION ON REACTION STRING COMPOSED OF BOND CLASSIFIED INTO GROUP (2) AND BOND CLASSIFIED INTO GROUP (3) ARRANGED ALTERNATELY

STORING THE INFORMATION ON RING STRUCTURES IN RECORDING MATERIAL

METHOD FOR PROCESSING INFORMATION ON CHEMICAL REACTIONS

This application is a continuation of application Ser. No. 903,154, filed Sept. 3, 1986, now abandoned.

BACKGROUNDS OF THE INVENTION

1. Field of the Invention

The present invention relates to a method for processing information on chemical reactions and more particularly, to a method for processing information on changes in the chemical structures of substances concerned with chemical reactions.

2. Description of the Prior Art

Various methods for recording structural information on chemical substances, particularly organic compounds have been proposed and attempted with the development of computers in recent years. A vast amount of organic compounds and organic reactions have been studied and worked out up to the present, and it is highly required that known chemical substances or chemical reactions are retrieved in a short time, or methods for the synthesis of new substances having the desired properties are found out, by effectively utilizing information on said known compounds and reactions. For this purpose, development of a new representation mode for chemical substances and chemical reactions is needed, which can be processed by computer (that is, which can be logically judged by computer) instead of an ordinary mode such as structural formula which can be readily treated by chemists.

Typical methods for recording chemical substances (methods for the representation or description of chemical substances) are a linear notation method such as WLN (Wiswesser Linear Notation) and a method using connection table. These methods are described in, for example, W. T. Wipke, S. R. Heller, R. J. Feldmann and E. Hyde (Eds.): "Computer Representation and Manipulation of Chemical Information", John Wiley and Sons, New York, 1974. The connection table is a list in which the kind of atoms and the kinds of neighbor atoms and bonds, etc. appeared in the structural formula of chemical substance are tabulated and the connection table has an advantage that chemical substances can be retrieved atom by atom as compared with the linear notation.

Further, methods for recording information on change in the chemical structures of substances (on chemical reactions) have been proposed, but a satisfactory representation method is not developed as yet. For instance, as methods for the description of chemical reactions, there are methods using a reaction code, such as a method described in J. Valls and O. Scheiner: "Chemical Information Systems", ed. by E. Ash and E. Hyde, Ellis Horwood Limited, 1975, p.241-258; a method described in M. A. Lobeck, Angew. Chem. Intern. Ed. Engl., 9, 578(1970); and a method described in H. J. Ziegler, J. Chem. Inf. Comput. Sci., 19, 141(1979). In these methods, a view of the representation for chemical reactions is fixed and hence, these methods have a disadvantage that any novel chemical reactions can not be described. Further, there are disadvantages that since structural information on chemical substances and information on structural changes thereof are recorded in a separate form, it is hard to make an effective information retrieval.

There are other known recording methods worked out for design of synthetic pathways of chemical substances, for instance, methods described in E. J. Corey, R. D. Cramer, J. Howe and W. J. Howe, J. Am. Chem. Soc., 94, 440(1972); and I. Ugi, J. Bauer, J. Braodt, J. Friedrich, J. Gasteiger, L. Jochum and W. Schubert, Angew. Chem. Intern. Ed. Engl., 18, 111(1979).

SUMMARY OF THE INVENTION

It is an object of the present invention to provide a novel processing method for extracting information on bond changes inherent to a reaction from information on chemical reactions.

It is another object of the present invention to provide a processing method for recording and storing information on bond changes inherent to a reaction on the basis of information on chemical reactions in a representation mode which can be processed by computer.

The present invention provides a method for processing information on chemical reactions of producing at least one product from at least one starting material, said information being given in the form of imaginary transition structures in which the starting material is topologically superposed upon the product and bonds are distinguished and classified into three categories of (1) bonds linking two nodes appearing both in the starting and product stages, (2) bonds linking two nodes appearing only in the starting stage and (3) bonds linking two nodes appearing only in the product stage, which comprises extracting from the imaginary transition structure a reaction string composed of said bonds (2) and said bonds (3) arranged alternately.

The present invention also provides a method for processing information on chemical reactions of producing at least one product from at least one starting material, said information being given in the form of connection tables containing information on nodes and bonds linking two nodes which are distinguished between the starting material and the product topologically superposed thereon and classified into three categories of (1) bonds linking two nodes appearing both in the starting and product stages, (2) bonds linking two nodes appearing only in the starting stage and (3) bonds linking two nodes appearing only in the product stage, which comprises extracting from the connection table information on a reaction string composed of said bonds (2) and said bonds (3) arranged alternately.

According to the present invention, information on bond changes inherent to reactions can be automatically obtained by subjecting information on chemical reactions inputted in the form of imaginary transition structure and/or connection table to appropriate processing.

The term "imaginary transition structure" (hereinafter referred to as ITS) used herein refers to two-dimensional or three-dimensional structural diagram (graph) wherein changes in substances participating in a chemical reaction are represented by distinguishing chemical bonds and classifying them into three categories comprising (1) bonds linking two adjacent nodes appearing only in the starting stage, (2) bonds linking two adjacent nodes appearing only in the product stage and (3) bonds linking two adjacent nodes appearing both in the starting and product stages. By using this structural diagram, the chemical reaction can be described by a from which is visually acceptable and readily comprehensible to chemists and technologists in accordance with the ordinary structural formula of chemical substance or the three-dimensional form thereof.

Connection table of ITS (hereinafter simply referred to as "connection table") is a table which essentially consists of a combination of the kind of nodes and the kinds of neighboring nodes and bonds linking these two nodes in a chemical reaction. By using this connection table, information on chemical reactions can be stored in a recording medium without requiring so large capacity.

In the above-mentioned imaginary transition structure and connection table, a chemical reaction can be basically described by a simple representation of nodes comprising atoms, groups, etc. and bonds linking two adjacent nodes. The bonds linking two nodes in the reaction system are distinguished and classified into said three categories of (1) to (3). Accordingly, only information on bond changes inherent to a chemical reaction (which is called "reaction string") can be taken out, when the imaginary transition structure or connection table is subjected to simple graphic processing or appropriate operational processing.

In the present invention, a reaction string represents a reaction type essential to a chemical reaction and the reaction string can be singly picked up as the representation inherent to a chemical reaction. This representation with the reaction strings is of great value, when individual chemical reactions or a series of chemical reactions are retrieved, studied and applied, and particularly organic synthesis reactions are done.

When information on reaction strings is obtained in the form of a two-dimensional or three-dimensional diagram in accordance with the imaginary transition structure, there are advantages that the information is visually acceptable and can be directly used in the practical field, because the obtained form is almost the same as the ordinary representation mode of chemical substances. When information on reaction strings is obtained in the form of a connection table, there are other advantages that comparison and collation with the reaction information denoted in the same form is easy and the obtained information can be stored in a computer without requiring a large capacity.

Further, information on reaction strings can be represented in the form of character, symbols or a combination thereof such as character string. When information on reaction strings is denoted in such a form, there are advantages that the information can be very simply denoted, the information can be easily registered in a computer without requiring a large capacity and the retrieval of chemical reactions can be made simply in a short time on the basis of the stored reaction information. It is also possible to store (enter), record and display the information on reaction strings denoted by character string, etc. in a combination with the reaction information denoted by the form of imaginary transition structure, connection table, etc. or with the substance information relating to reactions, and such a combination mode is very effective in the computer processing of chemical information.

Diagrams, connection tables and/or character strings with respect to the information on reaction strings can be stored (entered) in a computer, recorded on a paper, or displayed on a screen such as CRT.

Further, arbitrary transformation between the two-dimensional or three-dimensional diagram and the connection table of the reaction string is also possible so as to denote the information on reaction strings in any form, when the connection table contains information on space coordinate of each node. By using the registered diagrams, connection tables and/or character strings, chemical reactions can be retrieved and collated atom by atom.

Especially, when the information on reaction strings is registered in the form of the diagram in accordance with the imaginary transition structure or in the form of the connection table, not only individual reactions but also a plurality of consecutive reactions (multi-step reactions) can be tabulated by a table, and further, an arbitrary intermediate reaction or a series of synthesis reactions can be simply denoted. When the information on reaction strings is registered in the form of the connection table or the character string, information processing by computer is made easy and the registration of chemical reactions on a recording medium is made simple, so that the storage and the management of information can be readily conducted.

Therefore, the information retrieval of chemical reactions and chemical substances concerned therewith can be made effectively in a short time on the basis of the stored information on reaction strings, so that the time required for the collection of information on studies and investigations can be shortened, the amount of information can be increased and efficient researches can be achieved.

Furthermore, the combination of the information on reaction strings obtained by the method of the present invention with the already inputted reaction information and further with the substance information obtained from said reaction information, can be effectively applied to the fields of structural analysis of chemical substances, molecular modeling and heuristic analysis of organic synthesis, all of which are highly demanded by workers concerned with the manufacture of medicines. Further, the retrieval of substructures of chemical substances, correlation between structure and activity, automatic determination of chemical structure of unknown compounds, mechanistic evaluation for the reaction of complicated compounds under certain conditions and prediction of mechanism therefor can be made within a practically possible range in a short time.

BRIEF DESCRIPTION OF DRAWING

FIG. 1 illustrates a flow sheet for performing the method of the present invention.

DETAILED DESCRIPTION OF THE INVENTION

In the method for processing information on chemical reactions according to the present invention, there is conducted an operation for extracting only specific bonds from the reaction information recorded and stored in the form of imaginary transition structure and/or connection table which is represented by distinguishing bonds and classifying them into three categories, i.e., bonds linking two nodes appearing only in the starting stage, bonds linking two nodes appearing only in the product stage and bonds linking two nodes appearing both in the starting and product stages, whereby information on bond changes inherent to a chemical reaction (i.e. information on reaction string) can be obtained in the form of diagram, connection table and/or character string.

Now, the method of the present invention will be described by referring to the hydrolysis of ethyl acetate catalyzed by hydrochloric acid. The chemical reaction is represented by the following equation:

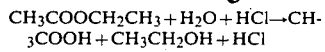 (Eq. 1)

An imaginary transition structure (ITS) of the reaction is denoted as follows:

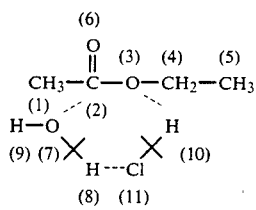 (ITS 1)

wherein (i) the symbol — indicates bonds appearing both in the starting and product stage,
(ii) the symbol + indicates bonds appearing only in the starting stage, and
(iii) the symbol . . . indicates bonds appearing only in the product stage.

Namely, the ITS is a diagram of two-dimension or three-dimension where bonds linking two adjacent nodes are distinguished between the starting materials and the products topologically superposed thereon and classified into said three categories (i) to (iii). The term "topologically superpose" used herein means that the chemical structures of the starting materials are combined with those of the products in such a manner that the nodes appearing in the former coincide with those appearing in the latter.

In the present invention, nodes of the substances concerned with a chemical reaction are allowed to be individual atoms contained in the starting and product stages, or groups such as functional groups, for example, methyl group (nodes 1 and 5), methylene group (node 4), etc. Part of nodes appearing in the starting and product stages may be omitted in representing the chemical reaction, and the invention is not restricted by the way of decision of nodes.

In the imaginary transition structure (ITS) according to the present invention, the notation for distinguishing the three kinds of bonds is by no means limited to the symbols defined by the above (i) to (iii), but the notation may be done by any means, for example: characters such as numerals (1, 2, 3, . . . ), colors (black, red, green, etc.), so long as users can judge the notation through the senses and it can be processed by computer.

In the invention hereinafter, (i) bonds (symbol —) appearing both in the starting and product stages are referred to as colorless bonds or "par-bonds",
(ii) bonds (symbol +) appearing only in the starting stage are referred to as "out-bonds", and
(iii) bonds (symbol . . . ) appearing only in the product stage are referred to as "in-bonds".

Further, the out- and in-bonds are together referred to as colored bond and all the bonds appeared in ITS (par-, out- and in-bonds) are referred to as "ITS bonds" or imaginary bonds.

The types of bonds appearing in the imaginary transition structure are shown in Table 1, wherein the numerical value in the horizontal means a characteristic of in-and-out.

TABLE 1

| Characteristic of In-and-out | $-3$ | $-2$ | $-1$ | $0$ | $+1$ | $+2$ | $+3$ |
|---|---|---|---|---|---|---|---|
| Single Bond | | | $+$ $(1-1)$ | $-$ $(1+0)$ | $\cdots$ $(0+1)$ | | |
| Double Bond | | $+$ $+$ $(2-2)$ | $+$ $+$ $(2-1)$ | $-$ $-$ $(2+0)$ | $-$ $-$ $(1+1)$ | $\cdots$ $\cdots$ $(0+2)$ | |
| Triple Bond | $+$ $+$ $+$ $(3-3)$ | $+$ $+$ $-$ $(3-2)$ | $+$ $-$ $-$ $(3-1)$ | $-$ $-$ $-$ $(3+0)$ | $-$ $-$ $-$ $(2+1)$ | $\cdots$ $-$ $-$ $(1+2)$ | $\cdots$ $\cdots$ $\cdots$ $(0+3)$ |

In Table 1, a bond represented by the symbol . . . is a single in-bond and denoted by a pair of integers (0+1) where 0 indicates that no bond is in the starting stage before reaction and +1 indicates that a bond is singly formed in the product stage after reaction. Similarly, a bond represented by the symbol + is a single out-bond and denoted by a pair of integers (1-1), which means that a single bond in the starting stage before reaction is cleaved (to disappear) in the product stage after reaction. A bond represented by a pair of integers (2-1) is a double bond singly cleaved and denoted by the symbol ±.

In this way, the kinds of bonds can be denoted by a pair of integers (a,b) wherein the interger a is bond multiplicity of the corresponding bond of the starting material and the integer b is difference in the bond multiplicity between the product and the starting material, which is referred to as "complex bond number" or "imaginary multiplicity". Even when the bond multiplicity is two or more, it can be simply denoted. If desired, the comma (,) of (a,b) may be deleted. This notation does not need large storage capacity and can be directly processed by computer, so that the notation is particularly preferred in the storage of data on chemical reactions.

Alternatively, chemical reactions are denoted by a connection table of ITS containing information on nodes, neighbor nodes and bonds linking said two nodes according to ITS.

Table 2 shows a connection table of the hydrolysis reaction of ester (Eq. 1). The connection table also contains information on two-dimensional coordinate (xy-coordinate) of each node.

As shown in Table 2, the connection table is a table in which all nodes, two-dimensional coordinates thereof (node 1 being the origin), all nodes neighboring on each node and the kinds of bonds linking two adjacent nodes are listed in order of node's number with respect to the starting stage (ethyl acetate, water and hydrochloric acid) and the product stage (acetic acid, ethanol and hydrochloric acid) concerned with the reaction.

TABLE 2

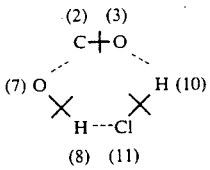

(RS 1)

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 1 | $CH_3$ | 0 | 0 | 2 (1 + 0) | | | |
| 2 | C | 200 | 0 | 1 (1 + 0) | 3 (1 − 1) | 6 (2 + 0) | 7 (0 + 1) |
| 3 | O | 400 | 0 | 2 (1 − 1) | 4 (1 + 0) | 10 (0 + 1) | |
| 4 | $CH_2$ | 600 | 0 | 3 (1 + 0) | 5 (1 + 0) | | |
| 5 | $CH_3$ | 800 | 0 | 4 (1 + 0) | | | |
| 6 | O | 200 | 200 | 2 (2 + 0) | | | |
| 7 | O | 200 | −200 | 2 (0 + 1) | 8 (1 − 1) | 9 (1 + 0) | |
| 8 | H | 341 | −341 | 7 (1 − 1) | 11 (0 + 1) | | |
| 9 | H | 59 | −341 | 7 (1 + 0) | | | |
| 10 | H | 541 | −141 | 3 (0 + 1) | 11 (1 − 1) | | |
| 11 | Cl | 541 | −341 | 8 (0 + 1) | 10 (1 − 1) | | |

The connection table of a reaction may be prepared from the imaginary transition structure. On the contrary, when the connection table contains information on the space coordinate of each node, the imaginary transition structure can be prepared therefrom. In other words, the imaginary transition structure and the connection table are in the relation of inside and outside of one registration and representation mode of the reaction information.

The information on the space coordinates of nodes may be incorporated in the connection table as described above. Further, information on stereochemistry and electronic charges of nodes; information on spectral and physical properties of substances related to chemical reactions; and information on reaction enthalpy, reaction temperature, reaction time, catalysts, reaction atmosphere, reaction media, yields, by-products, etc. may be combined to the imaginary transition structure and/or the connection table, if desired. Further, the imaginary transition structures and/or connection tables may be numbered one by one or reaction names may be registered together with them in order to facilitate the storage, management and retrieval of the reaction information.

Information on bond changes inherent to the reaction (i.e. reaction string) can be obtained in the form of diagram on the basis of the imaginary transition structure of the reaction in the following manner.

From the above-shown imaginary transition structure (ITS 1) which represents the hydrolysis reaction of ester:

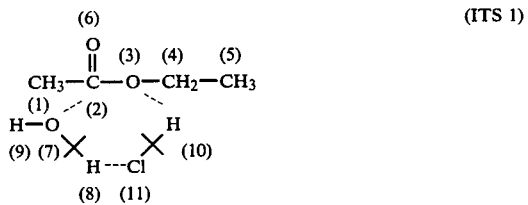

(ITS 1)

only colored bonds, i.e., out-bonds (symbol —) and in-bonds (symbol . . . ) are extracted, to obtain the following partial reaction structure:

In other words, the above diagram can be obtained by deleting the colorless bonds (symbol —) from ITS 1. However, when ITS bond is a multi-bond comprising a colorless bond(s) and a colored bond(s) (for example, ±, · · ·), said colorless bond(s) is left undeleted according to purpose.

In this reaction structure, nodes are connected with alternate in-bonds and out-bonds, and the reaction structure represents bond changes inherent to the reaction. In the present invention, the term "reaction string" (abbriviated to "RS") refers to said partial reaction structure. Namely, said RS 1 represents a reaction type specific to the hydrolysis of esters, being representation inherent to the reaction.

The reaction string can be obtained in the form of either two-dimensional diagram or three-dimensional diagram, depending upon whether ITS is two-dimensional or three-dimensional form.

When the information processing of the invention is conducted on the basis of ITS, the reaction string can be obtained in the form of diagram (two-dimensional or three-dimensional form) which can be visually acceptable and immediately understandable to chemists who intend to utilize information on chemical reactions.

The reaction string can be also denoted by characters, symbols or a combination thereof. For example, when simply denoting each node with the node's number, out-bonds with the symbol — and in-bonds with the symbol +, RS 1 can be denoted by the following character string:

(2)−(3)+(10)−(11)+(8)−(7)+(2)

The notation such as character string makes the information on reaction strings easy to store and record, and makes the computer processing such as information retrieval based on the stored information simple. Further, since such a notation requires not so much capacity, it can be used as additional information to the reaction information denoted by another form.

The information on reaction strings is obtained in the form of connection table on the basis of the connection table of the reaction in the following manner.

The reaction string can be obtained by detecting the colored bonds (bonds having b≠0) on the connection table of the reaction shown in Table 2 and then alternately picking out-bonds and in-bonds from the detected bonds in order of node's number, for example, atom by atom. When each bond linking two nodes is denoted by a pair of integers (a,b) wherein the integer a is bond multiplicity of the corresponding bond of the starting material and the integer b is difference in the bond multiplicity between the product and the starting material, the information on reaction strings is obtained as connection table by detecting all of (a,b) where b≠0 on the connection table of the reaction and rearranging these (a,b)'s in such a manner that node's numbers thereof are joined together in turn and the sign of the integers b is made to appear alternately in plus and minus value to prepare a connection table of the reaction string.

Table 3 shows the resulting connection table of the reaction string.

TABLE 3

| Node No. | Atom or Atomic Group | Neighbor Node (a, b) |
|---|---|---|
| 2 | C | — |
| 3 | O | 2 (1 − 1) |
| 10 | H | 3 (0 + 1) |
| 11 | Cl | 10 (1 − 1) |
| 8 | H | 11 (0 + 1) |
| 7 | O | 8 (1 − 1) |
| 2 | C | 7 (0 + 1) |

According to the information processing based on the connection table of the present invention, the information can be directly subjected to computer processing and information on the reaction string can be obtained simply in a short time. The obtained information on the reaction string can be stored without requiring a large capacity.

Further, the reaction string can be simply denoted by the character string on the basis of the obtained connection table.

When the connection table of the reaction string contains information on the space coordinate of each node, the structural diagram and the connection table can be transformed into each other. For example, after the extraction of a reaction string is executed on a connection table of the reaction, the obtained connection table of the reaction string can be transformed into a diagram.

Though one reaction string is contained in ITS 1, the number of reaction string may be two or more depending on reactions. For example, the Grignard reaction of ethyl acetate is represented by the following equation:

$$CH_3COOCH_2CH_3 + 2CH_3MgBr + 2H_2O \rightarrow (CH_3)_3COH + CH_3CH_2OH + 2MgBr(OH) \quad \text{(Eq. 2)}$$

An imaginary transition structure of the reaction can be denoted as follows:

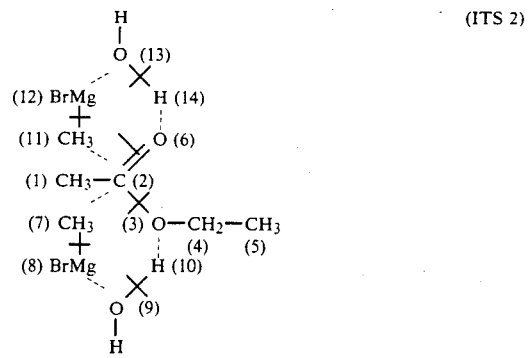
(ITS 2)

When ITS 2 is subjected to the above-described processing to extract reaction strings and denoted by character string, the following two reaction strings (RS 2) can be obtained:

(2)−(3)+(10)−(9)+(8)−(7)+(2)      2a (2)−(6)+(14)−(13)+(12)−(11)+(2)      2b

In this way, a reaction type specific to the Grignard reaction of Eq. 2 can be obtained.

Generally, organic reactions can be classified by the number of reaction strings. An organic reaction represented by ITS containing one reaction string is called a one-string reaction. Similarly, ITS containing two reaction strings and that containing three reaction strings are respectively called a two-string reaction and a three-string reaction. Accordingly, the hydrolysis of ester (Eq. 1) represented by ITS 1 is a one-string reaction, and the Grignard reaction (Eq. 2) represented by ITS 2 is a two-string reaction.

Thus, reactions can be classified by reaction string unit (referred to as "stringity"). Eq. 2 can be considered to be two consecutive reactions of the following Eqs. 2a and 2b:

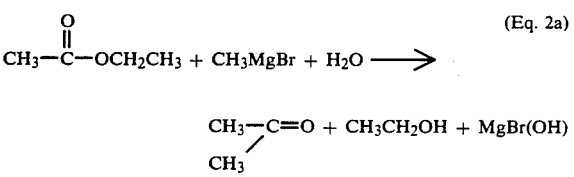
(Eq. 2a)

and

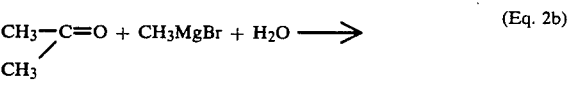
(Eq. 2b)

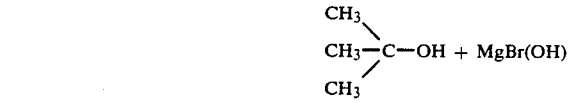

The imaginary transition structure corresponding to Eq. 2a is denoted as follows:

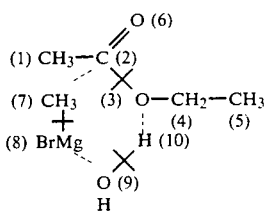
(ITS 2a)

The imaginary transition structure corresponding to Eq. 2b is denoted as follows:

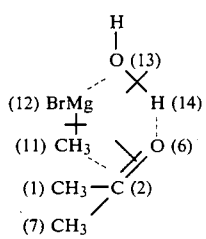
(ITS 2b)

Thus obtained diagrams, connection tables and/or character strings etc. of reaction strings may be independently stored (entered) in a computer, or may be recorded or displayed by use of an appropriate means.

The entry in a computer may be done by storing them in main storage thereof or in an appropriate recording medium (magnetic disk, optical disk or magnetic tape). The registered diagrams, connection tables and/or character strings can be recorded on a recording material such as plain paper by an appropriate recording device, or can be displayed on a colored CRT connected to the computer or electronic equipment.

The storing and recording of the information on reaction strings may be done in a combination of the diagram, the connection table and the character string. Alternatively, the information may be recorded or displayed together with the imaginary transition structure or the connection table of a reaction.

The information on the space coordinates of nodes may be incorporated in the connection table of reaction string (RS). Further, information on stereochemistry and electronic charges of nodes; information on spectral and physical properties of substances related to chemical reactions; and information on reaction enthalpy, reaction temperature, reaction time, catalysts, reaction atmosphere, reaction media, yields, by-products, etc. may be combined to the diagram, the connection table and/or the character string of RS, if desired.

In entering the diagrams, the connection tables and/or the character strings of RS in a computer, they may be numbered one by one or reaction names may be registered together with them in order to facilitate the storage, management and retrieval of the information on reaction strings.

When the information on reaction strings stored in the computer contains these additional information, the information can be widely used as data base in the fields of structure search systems, reaction search systems and design of organic synthesis pathways. Further, when the synthesis reaction is composed of multi-step reactions, they can be denoted by plural reaction strings integrating the multi-step reactions. That is, not only individual reactions but also the whole of complicated reactions such as those in the synthesis of organic compounds can be simply denoted and a part of these reactions can be extracted therefrom and denoted.

Furthermore, the use of a combination of the information on reaction strings obtained according to the present invention with the registrated reaction information or the substance information can bring about the further application to the chemical field utilizing computer such as molecular modeling according to the specific properties of substances, the design of synthetic pathways of organic compounds and the determination of the structures of unknown compounds.

The method for processing information on chemical reactions to obtain information on chemical substances (starting materials and products) relating to reactions on the basis of the imaginary transition structures and/or the connection tables thereof is described in more detail in our co-pending Japanese Patent Application No. 60(1985)-185386.

The following examples will further illustrate the method for processing information on chemical reactions according to the present invention.

EXAMPLE 1

Reaction for Addition of N-Butyl Lithium to Acetone

The reaction is represented by the schematic equation.

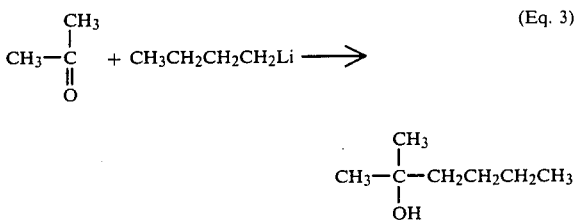
(Eq. 3)

The addition reaction is denoted by the following imaginary transition structure.

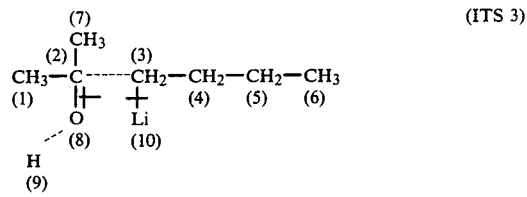
(ITS 3)

ITS 3 was subjected to the operation of extracting reaction string (RS) to obtain a reaction string in the form of a two-dimensional diagram.

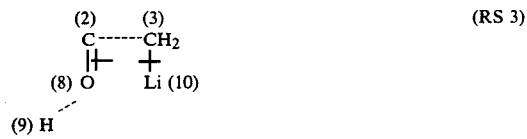
(RS 3)

RS 3 was also denoted by a character string:

(9)+(8)—(2)+(3)—(10)

A connection table corresponding to ITS 3 is set forth in Table 4.

TABLE 4

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 1 | $CH_3$ | 0 | 0 | 2 (1 + 0) | | | |
| 2 | C | 200 | 0 | 1 (1 + 0) | 3 (0 + 1) | 7 (1 + 0) | 8 (2 − 1) |
| 3 | $CH_2$ | 400 | 0 | 2 (0 + 1) | 4 (1 + 0) | 10 (1 − 1) | |
| 4 | $CH_2$ | 600 | 0 | 3 (1 + 0) | 5 (1 + 0) | | |
| 5 | $CH_2$ | 800 | 0 | 4 (1 + 0) | 6 (1 + 0) | | |
| 6 | $CH_3$ | 1000 | 0 | 5 (1 + 0) | | | |
| 7 | $CH_3$ | 200 | 200 | 2 (1 + 0) | | | |
| 8 | O | 200 | −200 | 2 (2 − 1) | 9 (0 + 1) | | |
| 9 | H | 59 | −341 | 8 (0 + 1) | | | |
| 10 | Li | 400 | −200 | 3 (1 − 1) | | | |

The connection table was subjected to the operation of RS extraction to obtain a connection table of RS. The result is set forth in Table 5.

TABLE 5

| Node No. | Atom or Atomic Group | Neighbor Node (a, b) |
|---|---|---|
| 9 | H | — |
| 8 | O | 9 (0 + 1) |
| 2 | C | 8 (2 − 1) |
| 3 | $CH_2$ | 2 (0 + 1) |
| 10 | Li | 3 (1 − 1) |

EXAMPLE 2

Acylation Reaction by Friedel-Crafts Reaction

The reaction is represented by the schematic equation.

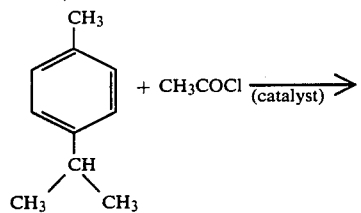   (Eq. 4)

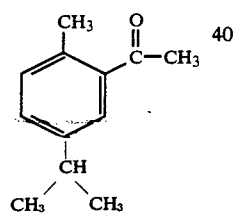

The Friedel-Crafts reaction is denoted by the following imaginary transition structure.

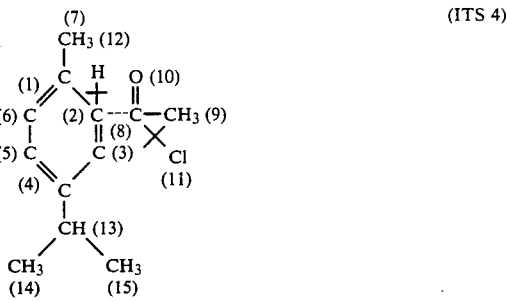   (ITS 4)

ITS 4 was subjected to the operation of RS extraction to obtain a reaction string in the form of a two-dimensional diagram.

   (RS 4)

RS 4 was also denoted by a character string:

(12)−(2)+(8)−(11)

A connection table corresponding to ITS 4 is set forth in Table 6.

TABLE 6

| Node | | Coordinate | | Neighbor 1 | Neighbor 2 | Neighbor 3 | Neighbor 4 |
|---|---|---|---|---|---|---|---|
| No. | Kind | X | Y | Node (a, b) | Node (a, b) | Node (a, b) | Node (a, b) |
| 1 | C | 0 | 200 | 2 (1 + 0) | 6 (2 + 0) | 7 (1 + 0) | |
| 2 | C | 173 | 100 | 1 (1 + 0) | 3 (2 + 0) | 8 (0 + 1) | 12 (1 − 1) |
| 3 | C | 173 | −100 | 2 (2 + 0) | 4 (1 + 0) | | |
| 4 | C | 0 | −200 | 3 (1 + 0) | 5 (2 + 0) | 13 (1 + 0) | |
| 5 | C | −173 | −100 | 4 (2 + 0) | 6 (1 + 0) | | |
| 6 | C | −173 | 100 | 1 (2 + 0) | 5 (1 + 0) | | |
| 7 | $CH_3$ | 0 | 400 | 1 (1 + 0) | | | |
| 8 | C | 373 | 100 | 2 (0 + 1) | 9 (1 + 0) | 10 (2 + 0) | 11 (1 − 1) |
| 9 | $CH_3$ | 573 | 100 | 8 (1 + 0) | | | |
| 10 | O | 373 | 300 | 8 (2 + 0) | | | |
| 11 | Cl | 373 | −100 | 8 (1 − 1) | | | |
| 12 | H | 273 | 273 | 2 (1 − 1) | | | |
| 13 | CH | 0 | −400 | 4 (1 + 0) | 14 (1 + 0) | 15 (1 + 0) | |
| 14 | $CH_3$ | −100 | −573 | 13 (1 + 0) | | | |
| 15 | $CH_3$ | 100 | −573 | 13 (1 + 0) | | | |

The connection table was subjected to the operation of RS extraction to obtain a connection table of RS. The result is set forth in Table 7.

TABLE 7

| Node No. | Atom or Atomic Group | Neighbor Node (a, b) |
|---|---|---|
| 12 | H | — |
| 2 | C | 12 (1 − 1) |
| 8 | C | 2 (0 + 1) |
| 11 | Cl | 8 (1 − 1) |

EXAMPLE 3

Beckmann Rearrangement

The reaction is represented by the schematic equation.

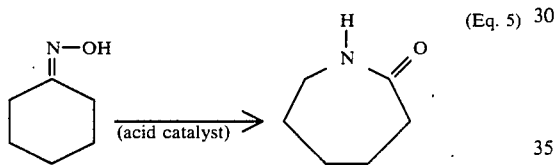

(Eq. 5)

The Beckmann rearrangement is denoted by the following imaginary transition structure.

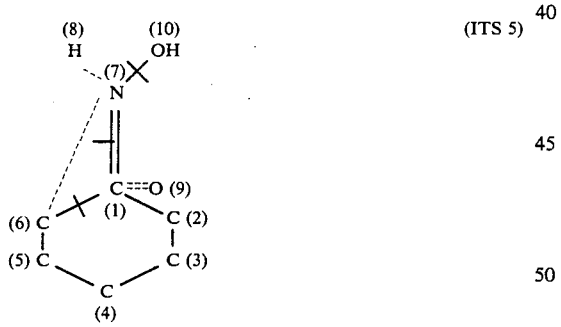

(ITS 5)

ITS 5 was subjected to the operation of RS extraction to obtain reaction strings in the form of a two-dimensional diagram.

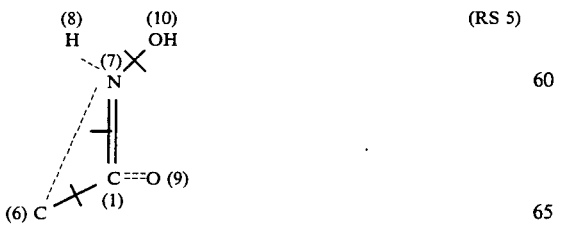

(RS 5)

RS 5 was also denoted by character strings:

(10)−(7)+(6)−(1)+(9)

(8)+(7)−(1)+(9)

Thus, it was clear to be a two-string reaction.

A connection table corresponding to ITS 5 is set forth in Table 8.

TABLE 8

| Node No. | Kind | Coordinate X | Y | Neighbor 1 Node (a, b) | Neighbor 2 Node (a, b) | Neighbor 3 Node (a, b) | Neighbor 4 Node (a, b) |
|---|---|---|---|---|---|---|---|
| 1 | C | 0 | 200 | 2 (1 + 0) | 6 (1 − 1) | 7 (2 − 1) | 9 (0 + 2) |
| 2 | C | 173 | 100 | 1 (1 + 0) | 3 (1 + 0) | | |
| 3 | C | 173 | −100 | 2 (1 + 0) | 4 (1 + 0) | | |
| 4 | C | 0 | −200 | 3 (1 + 0) | 5 (1 + 0) | | |
| 5 | C | −173 | −100 | 4 (1 + 0) | 6 (1 + 0) | | |
| 6 | C | −173 | 100 | 1 (1 − 1) | 5 (1 + 0) | 7 (0 + 1) | |
| 7 | N | 0 | 400 | 1 (2 − 1) | 6 (0 + 1) | 8 (0 + 1) | 10 (1 − 1) |
| 8 | H | −100 | 573 | 7 (0 + 1) | | | |
| 9 | O | 173 | 300 | 1 (0 + 2) | | | |
| 10 | OH | 100 | 573 | 7 (1 − 1) | | | |

The connection table was subjected to the operation of RS extraction to obtain connection tables of RS. The results are respectively set forth in Tables 9 and 10.

TABLE 9

| Node No. | Atom or Atomic Group | Neighbor Node (a, b) |
|---|---|---|
| 10 | OH | — |
| 7 | N | 10 (1 − 1) |
| 6 | C | 7 (0 + 1) |
| 1 | C | 6 (1 − 1) |
| 9 | O | 1 (0 + 2) |

TABLE 10

| Node No. | Atom or Atomic Group | Neighbor Node (a, b) |
|---|---|---|
| 8 | H | — |
| 7 | N | 8 (0 + 1) |
| 1 | C | 7 (2 − 1) |
| 9 | O | 1 (0 + 2) |

EXAMPLE 4

Methylation Reaction of Cycloheptanone

The reaction is represented by the schematic equation.

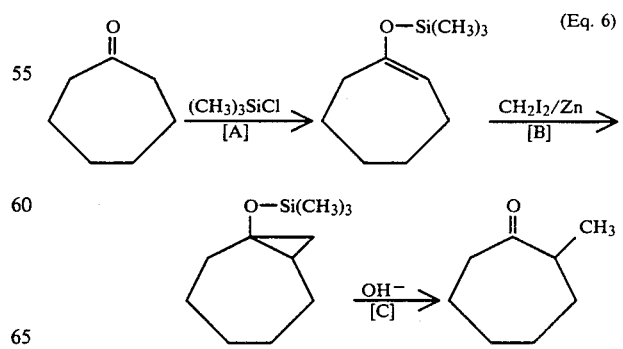

(Eq. 6)

(1) The reaction at step [A] is denoted by the following imaginary transition structure.

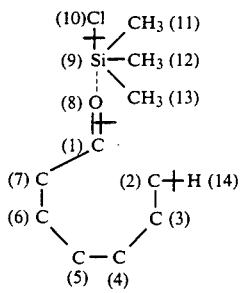

(ITS 6)

ITS 6 was subjected to the operation of RS extraction to obtain a reaction string in the form of a two-dimensional diagram.

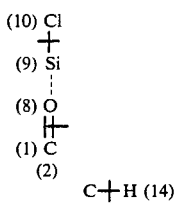

(RS 6)

RS 6 was also denoted by a character string:

(10)−(9)+(8)−(1)+(2)−(14)

A connection table corresponding to ITS 6 is set forth in Table 11.

TABLE 11

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a, b) | Node (a, b) | Node (a, b) | Node (a, b) | Node (a, b) |
| 1 | C | 0 | 200 | 2 (1 + 1) | 7 (1 + 0) | 8 (2 − 1) | | |
| 2 | C | 173 | 100 | 1 (1 + 1) | 3 (1 + 0) | 14 (1 − 1) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 − 1) | 9 (0 + 1) | | | |
| 9 | Si | 0 | 600 | 8 (0 + 1) | 10 (1 − 1) | 11 (1 + 0) | 12 (1 + 0) | 13 (1 + 0) |
| 10 | Cl | 0 | 800 | 9 (1 − 1) | | | | |
| 11 | CH3 | 100 | 773 | 9 (1 + 0) | | | | |
| 12 | CH3 | 173 | 700 | 9 (1 + 0) | | | | |
| 13 | CH3 | 200 | 600 | 9 (1 + 0) | | | | |
| 14 | H | 314 | −41 | 2 (1 − 1) | | | | |

The connection table was subjected to the operation of RS extraction to obtain a connection table of RS. The result is set forth in Table 12.

TABLE 12

| Node No. | Atom or Atomic Group | Neighbor Node (a, b) |
|---|---|---|
| 10 | Cl | — |
| 9 | Si | 10 (1 − 1) |

TABLE 12-continued

| Node No. | Atom or Atomic Group | Neighbor Node (a, b) |
|---|---|---|
| 8 | O | 9 (0 + 1) |
| 1 | C | 8 (2 − 1) |
| 2 | C | 1 (1 + 1) |
| 14 | H | 2 (1 − 1) |

(2) The reaction at step [B] is denoted by the following imaginary transition structure.

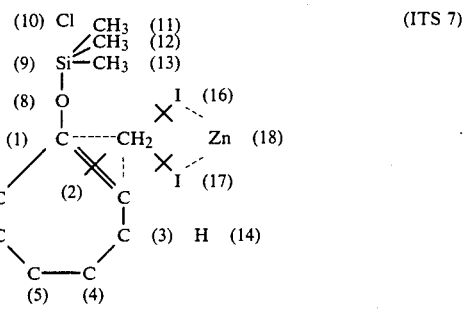

(ITS 7)

ITS 7 was subjected to the operation of RS extraction to obtain a reaction string in the form of a two-dimensional diagram.

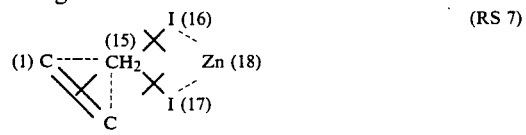

(RS 7)

RS 7 was also denoted by a character string:

(18)+(16)−(15)+(1)−(2)+(15)−(17)+(18)

A connection table corresponding to ITS 7 is set forth in Table 13.

TABLE 13

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a, b) | Node (a, b) | Node (a, b) | Node (a, b) | Node (a, b) |
| 1 | C | 0 | 200 | 2 (2 − 1) | 7 (1 + 0) | 8 (1 + 0) | 15 (0 + 1) | |
| 2 | C | 173 | 100 | 1 (2 − 1) | 3 (1 + 0) | 15 (0 + 1) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 + 0) | | | |

TABLE 13-continued

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a, b) | Node (a, b) | Node (a, b) | Node (a, b) | Node (a, b) |
| 9 | Si | 0 | 600 | 8 (1 + 0) | 11 (1 + 0) | 12 (1 + 0) | 13 (1 + 0) | |
| 10 | Cl | 0 | 800 | | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | | | | | |
| 15 | CH$_2$ | 200 | 200 | 1 (0 + 1) | 2 (0 + 1) | 16 (1 − 1) | 17 (1 − 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |

The connection table was subjected to the operation of RS extraction to obtain a connection table of RS. The result is set forth in Table 14.

TABLE 14

| Node No. | Atom or Atomic Group | Neighbor Node (a, b) |
|---|---|---|
| 18 | Zn | — |
| 16 | I | 18 (0 + 1) |
| 15 | CH$_2$ | 16 (1 − 1) |
| 1 | C | 15 (0 + 1) |
| 2 | C | 1 (2 − 1) |
| 15 | CH$_2$ | 2 (0 + 1) |
| 17 | I | 15 (1 − 1) |
| 18 | Zn | 17 (0 + 1) |

(3) The reaction at step [C] is denoted by the following imaginary transition structure.

ITS 8 was subjected to the operation of RS extraction to obtain a reaction string in the form of a two-dimensional diagram.

(RS 8)

$$\begin{array}{c}(20)\,OH\text{---}Si\,(9)\\+\\(8)\,O\quad H\,(19)\\|\\(1)\,C\!+\!CH_2\,(15)\end{array}$$

RS 8 was also denoted by a character string:

$(20)+(9)-(8)+(1)-(15)+(19)$

A connection table corresponding to ITS 8 is set forth in Table 15.

TABLE 15

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a, b) | Node (a, b) | Node (a, b) | Node (a, b) | Node (a, b) |
| 1 | C | 0 | 200 | 2 (1 + 0) | 7 (1 + 0) | 8 (1 + 1) | 15 (1 − 1) | |
| 2 | C | 173 | 100 | 1 (1 + 0) | 3 (1 + 0) | 15 (1 + 0) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 − 1) | | | |
| 9 | Si | 0 | 600 | 8 (1 − 1) | 11 (1 + 0) | 12 (1 + 0) | 13 (1 + 0) | 20 (0 + 1) |
| 10 | Cl | 0 | 800 | | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | | | | | |
| 15 | CH$_2$ | 200 | 200 | 1 (1 − 1) | 2 (1 + 0) | 19 (0 + 1) | | |
| 16 | I | 373 | 300 | 18 (1 + 0) | | | | |
| 17 | I | 373 | 100 | 18 (1 + 0) | | | | |
| 18 | Zn | 546 | 200 | 16 (1 + 0) | 17 (1 + 0) | | | |
| 19 | H | 200 | 400 | 15 (0 + 1) | | | | |
| 20 | OH | −200 | 600 | 9 (0 + 1) | | | | |

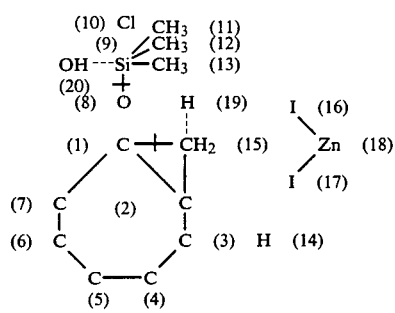

(ITS 8)

The connection table was subjected to the operation of RS extraction to obtain a connection table of RS. The result is set forth in Table 16.

TABLE 16

| Node No. | Atom or Atomic Group | Neighbor Node (a, b) |
|---|---|---|
| 20 | OH | — |
| 9 | Si | 20 (0 + 1) |
| 8 | O | 9 (1 − 1) |
| 1 | C | 8 (1 + 1) |
| 15 | CH$_2$ | 1 (1 − 1) |
| 19 | H | 15 (0 + 1) |

(4) The reaction at steps [A] and [B] represented by the schematic equation:

(Eq. 6')  (14)−(2)+(15)−(17)+(18)

A connection table corresponding to ITS 9 is set forth in Table 17.

TABLE 17

| Node No. | Kind | Coordinate X | Coordinate Y | Neighbor 1 Node (a, b) | Neighbor 2 Node (a, b) | Neighbor 3 Node (a, b) | Neighbor 4 Node (a, b) | Neighbor 5 Node (a, b) |
|---|---|---|---|---|---|---|---|---|
| 1 | C | 0 | 200 | 2 (1 + 0) | 7 (1 + 0) | 8 (2 − 1) | 15 (0 + 1) | |
| 2 | C | 173 | 100 | 1 (1 + 0) | 3 (1 + 0) | 14 (1 − 1) | 15 (0 + 1) | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 − 1) | 9 (0 + 1) | | | |
| 9 | Si | 0 | 600 | 8 (0 + 1) | 10 (1 − 1) | 11 (1 + 0) | 12 (1 + 0) | 13 (1 + 0) |
| 10 | Cl | 0 | 800 | 9 (1 − 1) | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | 2 (1 − 1) | | | | |
| 15 | CH$_2$ | 200 | 200 | 1 (0 + 1) | 2 (0 + 1) | 16 (1 − 1) | 17 (1 − 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |

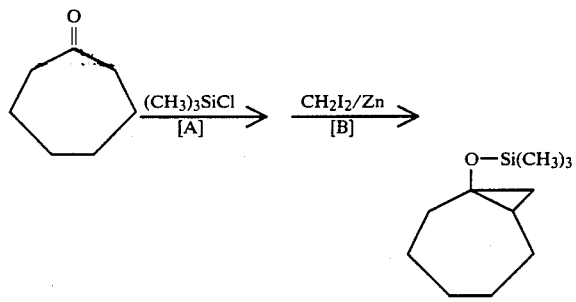

is denoted by the following imaginary transition structure.

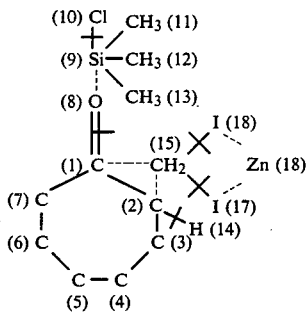
(ITS 9)

ITS 9 was subjected to the operation of RS extraction to obtain reaction strings in the form of a two-dimensional diagram.

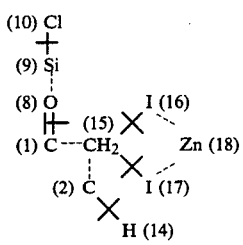
(RS 9)

RS 9 was also denoted by character strings:

(10)−(9)+(8)−(1)+(15)−(16)+(18)

The connection table was subjected to the operation of RS extraction to obtain connection tables of RS. The results are respectively set forth in Tables 18 and 19.

TABLE 18

| Node No. | Atom or Atomic Group | Neighbor Node (a, b) |
|---|---|---|
| 10 | Cl | — |
| 9 | Si | 10 (1 − 1) |
| 8 | O | 9 (0 + 1) |
| 1 | C | 8 (2 − 1) |
| 15 | CH$_2$ | 1 (0 + 1) |
| 16 | I | 15 (1 − 1) |
| 18 | Zn | 16 (0 + 1) |

TABLE 19

| Node No. | Atom or Atomic Group | Neighbor Node (a, b) |
|---|---|---|
| 14 | H | — |
| 2 | C | 14 (1 − 1) |
| 15 | CH$_2$ | 2 (0 + 1) |
| 17 | I | 15 (1 − 1) |
| 18 | Zn | 17 (0 + 1) |

(5) The reaction at steps [A], [B] and [C] represented by the schematic equation:

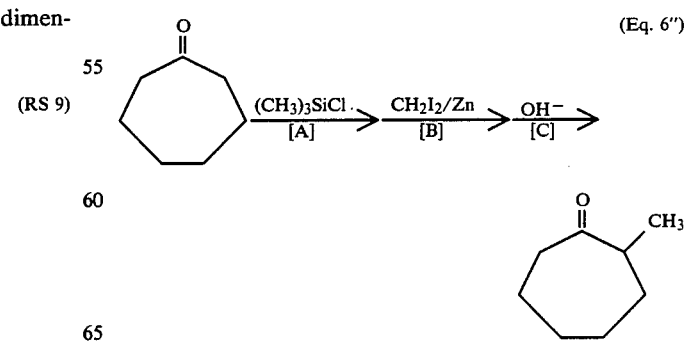
(Eq. 6'')

is denoted by the following imaginary transition structure.

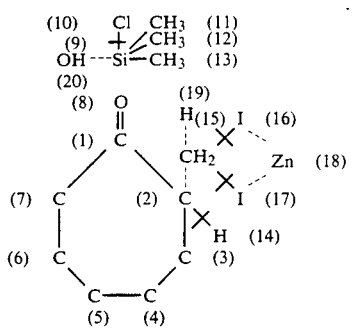

(ITS 10)

ITS 10 was subjected to the operation of RS extraction to obtain reaction strings in the form of a two-dimensional diagram.

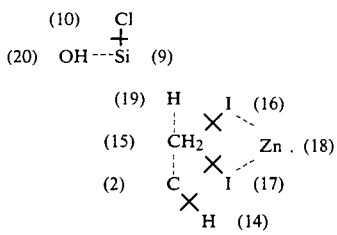

(RS 10)

RS 10 was also denoted by character strings:

(19)+(15)−(16)+(18)

(14)−(2)+(15)−(17)+(18)

(10)−(9)+(20)

A connection table corresponding to ITS 10 is set forth in Table 20.

TABLE 20

| Node No. | Kind | Coordinate X | Y | Neighbor 1 Node (a, b) | Neighbor 2 Node (a, b) | Neighbor 3 Node (a, b) | Neighbor 4 Node (a, b) | Neighbor 5 Node (a, b) |
|---|---|---|---|---|---|---|---|---|
| 1 | C | 0 | 200 | 2 (1 + 0) | 7 (1 + 0) | 8 (2 + 0) | | |
| 2 | C | 173 | 100 | 1 (1 + 0) | 3 (1 + 0) | 14 (1 − 1) | 15 (0 + 1) | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 + 0) | | | | |
| 9 | Si | 0 | 600 | 10 (1 − 1) | 11 (1 + 0) | 12 (1 + 0) | 13 (1 + 0) | 20 (0 + 1) |
| 10 | Cl | 0 | 800 | 9 (1 − 1) | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | 2 (1 − 1) | | | | |
| 15 | CH$_2$ | 200 | 200 | 2 (0 + 1) | 16 (1 − 1) | 17 (1 − 1) | 19 (0 + 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |
| 19 | H | 200 | 400 | 15 (0 + 1) | | | | |
| 20 | OH | −200 | 600 | 9 (0 + 1) | | | | |

The connection table was subjected to the operation of RS extraction to obtain connection tables of RS. The results are respectively set forth in Tables 21 to 23.

TABLE 21

| Node No. | Atom or Atomic Group | Neighbor Node (a, b) |
|---|---|---|
| 19 | H | — |
| 15 | CH$_2$ | 19 (0 + 1) |

TABLE 21-continued

| Node No. | Atom or Atomic Group | Neighbor Node (a, b) |
|---|---|---|
| 16 | I | 15 (1 − 1) |
| 18 | Zn | 16 (0 + 1) |

TABLE 22

| Node No. | Atom or Atomic Group | Neighbor Node (a, b) |
|---|---|---|
| 14 | H | — |
| 2 | C | 14 (1 − 1) |
| 15 | CH$_2$ | 2 (0 + 1) |
| 17 | I | 15 (1 − 1) |
| 18 | Zn | 17 (0 + 1) |

TABLE 23

| Node No. | Atom or Atomic Group | Neighbor Node (a, b) |
|---|---|---|
| 10 | Cl | — |
| 9 | Si | 10 (1 − 1) |
| 20 | OH | 9 (0 + 1) |

I claim:

1. A method of storing information for an organic chemical reaction in which a reaction of at least one starting material to give at least one reaction product is involved; which comprises the steps of:

(a) topologically superposing a chemical structural formula of the starting material or a combination of chemical structural formulae of the starting materials on a chemical structural formula of the reaction product or a combination of chemical structural formulae of the reaction products to produce an imaginary transition structure;

(b) classifying each bond linking two nodes of the imaginary transition structure into the following three groups; (1) bond linking two nodes appearing both in the formulae of the starting material and the reaction product, (2) bond linking two nodes appearing only in the formula of the starting material, and (3) bond linking two nodes appearing only in the formula of the reaction product;

(c) representing nodes and bonds classified in step (b) in the form of a connection table;

(d) extracting from the connection table information on a reaction string composed of the bonds classified into the group (2) and the bonds classified into the group (3) arranged alternately; and (e) storing the information on the reaction string in a recording material.

2. The method of claim 1, wherein the step (b) of classifying each bond is performed by denoting the bond linking two nodes in the connection table using pairs of integers (a, b), in which the integer "a" is bond multiplicity of the corresponding bond of the formula of the starting material and the integer "b" is the difference in the bond multiplicity between the formulae of the product and the starting material, and the step further includes detecting all of bonds where b=o from the connection table and arranging these bonds in such manner that nodes are connected in order and the integers "b" thereof have alternately a positive value and a negative value.

3. The method of claim 1, wherein the information on a reaction string is stored in the form of a connection table.

4. The method of claim 1, wherein the information on a reaction string is stored in the form of characters, symbols or a combination thereof.

5. The method of claim 1, wherein the step (c) of representing nodes and bonds is performed to give a connection table having two-dimensional or three-dimensional coordinates of nodes, and the information on a reaction string is stored in a two-dimensional or three-dimensional form.

6. The method of claim 1, wherein the step of topologically superposing the chemical structureal formulae is performed on a display.

7. The method of claim 1, wherein the step of classifying each bond is performed by denoting the bond linking two nodes in the connection table using pairs of integers:

(1+0) which denotes a bond having one bond of (1) only;

(2+0) which denotes a bond having two bonds of (1) only;

(3+0) which denotes a bond having three bonds of (1) only;

(1−1) which denotes a bond having one bond of (2) only;

(2−1) which denotes a bond having one bond of (1) and one bond of (2) only;

(3−1) which denotes a bond having two bonds of (1) and one bond of (2) only;

(2−2) which denotes a bond having two bonds of (2) only;

(3−2) which denotes a bond having one bond of (1) and two bonds of (2) only;

(3−3) which denotes a bond having three bonds of (2) only;

(0+1) which denotes a bond having one bond of (3) only;

(1+1) which denotes a bond having one bond of (1) and one bond of (3) only;

(2+1) which denotes a bond having two bonds of (1) and one bond of (3) only;

(0+2) which denotes a bond having two bonds of (3) only;

(1+2) which denotes a bond having one bond of (1) and two bonds of (3) only;

(0+3) which denotes a bond having three bonds of (3) only.

* * * * *